United States Patent [19]

Seele et al.

[11] Patent Number: 5,122,531
[45] Date of Patent: Jun. 16, 1992

[54] VINYLAZOLES AND THE USE THEREOF FOR CROP PROTECTION

[75] Inventors: Rainer Seele, Fussgoenheim; Wolfgang Rohr, Wachenheim; Bernhard Zipperer, Dirmstein; Stefan Karbach, Neustadt; Lothar Rueb, Speyer; Eberhard Ammermann, Ludwigshafen; Gisela Lorenz, Neustadt; Wilhelm Rademacher; Johann Jung, both of Limburgerhof, all of Fed. Rep. of Germany

[73] Assignee: BASF Aktiengesellschaft, Ludwigshafen, Fed. Rep. of Germany

[21] Appl. No.: 586,154

[22] Filed: Sep. 21, 1990

[30] Foreign Application Priority Data

Sep. 28, 1989 [DE] Fed. Rep. of Germany ....... 3932387

[51] Int. Cl.$^5$ ................. A01N 43/653; C07D 249/08
[52] U.S. Cl. .................................... 514/383; 514/184; 548/101; 548/267.2; 548/268.4
[58] Field of Search ................. 548/268.4, 101, 267.2; 514/383, 184

[56] References Cited

U.S. PATENT DOCUMENTS 4,360,528  11/1982  Jäger et al. ............... 548/268.4

FOREIGN PATENT DOCUMENTS 44993    2/1982  European Pat. Off. ......... 548/268.4
0094564  11/1983  European Pat. Off. .

*Primary Examiner*—Patricia L. Morris
*Attorney, Agent, or Firm*—Oblon, Spivak, McClelland, Maier & Neustadt

[57] ABSTRACT

Vinylazoles of the general formula I

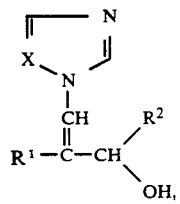

where $R^1$ and $R^2$ are alkyl, cycloalkyl, tetrahydropyranyl, pyridyl, naphthyl, biphenyl or phenyl, these radicals being substituted or unsubstituted, X is CH or N, and plant-tolerated acid addition salts and metal complexes thereof, and crop protection agents containing these compounds.

8 Claims, No Drawings

VINYLAZOLES AND THE USE THEREOF FOR CROP PROTECTION

The present invention relates to novel azole compounds, processes for the preparation thereof and fungicides and growth regulators containing these.

The use as fungicides of 1-(1,2,4-triazol-1-yl)- -(2-1 -(4-chlorophenyl)-3-(2,4-dichlorophenyl)-1-propen-3-ol and 1-(1,2,4-triazol-1-yl)-2-(4-chlorophenyl)-3-phenyl-1-propen-3-ol has been disclosed (EP 23286). However, the fungicidal effects are not satisfactory in all cases.

We have now found that vinylazoles of the formula I

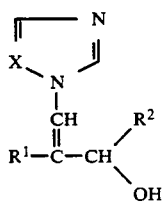

where $R^1$ and $R^2$ are identical or different and each is $C_1$–$C_8$-alkyl, $C_3$–$C_8$-cycloalkyl, tetrahydropyranyl, pyridyl, naphthyl, biphenylyl or phenyl, it being possible for these radicals to be substituted once to three times by halogen, nitro, phenoxy, amino, alkyl, alkoxy or haloalkyl of 1 to 4 carbon atoms in each case, and X is CH or N, and the acid addition salts or metal complexes thereof which are tolerated by plants, apart from the compounds where A is phenyl which is unsubstituted or substituted by chlorine when B is phenyl which is unsubstituted or substituted by chlorine in the 4 position or 2,4 positions, have a better fungicidal and growth regulating effect than known azole compounds.

The compounds of the formula I contain asymmetric carbon atoms and may thus exist as enantiomers and diastereomers. The diastereomers of the compounds according to the invention can be isolated in pure form from mixtures thereof in a conventional manner, for example on the basis of solubility differences or by column chromatography. The racemates of the compounds according to the invention can be resolved by conventional methods, for example salt formation with an optically active acid, separation of the diastereomeric salts and liberation of the enantiomers with a base. It is possible to use the pure diastereomers or enantiomers, as well as the mixtures thereof produced in the synthesis, as fungicides and growth regulators. The invention relates to all these compounds.

Examples of $R^1$ and $R^2$ are $C_1$–$C_8$-alkyl, especially $C_1$–$C_4$-alkyl such as methyl, ethyl, isopropyl, n-propyl, n-butyl, sec-butyl, tert-butyl, n-pentyl, neopentyl, 1-naphthyl, 2-naphthyl, p-biphenylyl, phenyl, halophenyl such as 2-chlorophenyl, 2-fluorophenyl, 2-bromophenyl, 3-chlorophenyl, 3-bromophenyl, 3-fluorophenyl, 4-fluorophenyl, 4-chlorophenyl, 4-bromophenyl, 2,4-dichlorophenyl, 2,3-dichlorophenyl, 2,5-dichlorophenyl, 2,6-dichlorophenyl, 2-chloro-6-fluorophenyl, 2-chloro-4-fluorophenyl, $C_1$–$C_4$-alkoxyphenyl, such as 2-methoxyphenyl, 3-methoxyphenyl, 4-methoxyphenyl, 2,4-dimethoxyphenyl, $C_1$–$C_4$-alkylphenyl, such as 4-ethylphenyl, 4-isopropylphenyl, 4-tert.-butylphenyl, 4-tert.-butyloxyphenyl, 2-chloro-6-methylphenyl, 3,4-dimethoxyphenyl, 3-phenoxyphenyl, 4-phenoxyphenyl, 3-nitrophenyl, 4-nitrophenyl, 3-aminophenyl, 4-aminophenyl, 2-trifluoromethylphenyl, 3-trifluoromethylphenyl, 4-trifluoromethylphenyl, 3-pyridyl, tetrahydropyranyl, $C_3$–$C_6$-cycloalkyl, such as cyclopropyl, cyclopentyl, cyclohexyl.

$R^1$ cannot be phenyl, monochlorophenyl or dichlorophenyl when $R^2$ is phenyl, 4-chlorophenyl or 2,4-dichlorophenyl.

$R^2$ is preferably phenyl substituted in the 2 position.

Examples of acid addition salts are the hydrochlorides, bromides, sulfates, nitrates, phosphates, oxalates or dodecylbenzenesulfonates. The activity of the salts derives from the cation so that the nature of the anion is generally inmaterial. The salts of the active compounds according to the invention are prepared by reacting the vinylazoles (I) with suitable acids.

Metal complexes of the active compounds I or salts thereof can be formed with, for example, copper, zinc, tin, manganese, iron, cobalt or nickel by reacting the vinylazole derivatives with the appropriate metal salts The compounds of the formula I can be prepared by rearranging a compound of the formula II

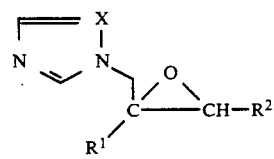

where $R^1$, $R^2$ and X have the meanings indicated above, into the vinylazole in the presence of a base.

The reaction is carried out in the presence or absence of a solvent or diluent with the addition of an inorganic or organic base at from 10° to 120° C.

The preferred solvents and diluents include ketones such as acetone, methyl ethyl ketone or cyclohexanone, nitriles such as acetonitrile or propionitrile, alcohols such as methanol, ethanol, iso-propanol, n-butanol or glycol, ethers such as tetrahydrofuran, diethyl ether, dimethoxyethane, dioxane or diisopropyl ether, amides such as dimethylformamide, dimethylacetamide or N-methylpyrrolidone, sulfolane or mixtures thereof.

Examples of suitable bases are alkali metal hydroxides such as lithium, sodium or potassium hydroxide, alkali metal hydrides such as lithium, sodium and potassium hydride, alkali metal amides such as those of sodium and potassium, alkali metal carbonates such as sodium or potassium carbonate or sodium or potassium bicarbonate, also sodium or potassium tert-butoxide and sodium or potassium methanolate.

The reaction is generally carried out at from 20° to 150° C.

The starting compounds II can be prepared by conventional methods (see EP 94564 and EP 196038).

EXAMPLES

The examples which follow illustrate the preparation of the active compounds

EXAMPLE 1

1-(1,2,4-Triazol-1-yl)-2-(4-chlorophenyl)-3-(2-trifluoromethylphenyl)-1-propen-3-ol

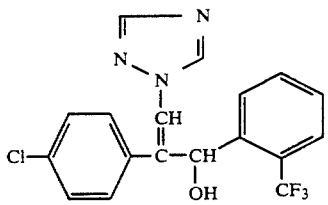

4 g of 2-(1,2,4-triazol-1-ylmethyl)-2-(4-chlorophenyl)-3-(2-trifluoromethylphenyl)oxirane are dissolved in 80 ml of methanol and, after addition of 1.2 g of sodium methylate, refluxed for one hour. The solution is then cooled to room temperature (20° C.), 50 ml of water are added and the mixture is extracted by shaking several times with methyl tert-butyl ether. The isolated organic phase is washed twice with water, dried over sodium sulfate and concentrated, resulting in 3.8 g (95 %) of 1-(1,2,4-triazol-1-yl)-2-(4-chlorophenyl)-3-(2-trifluoromethylphenyl)-1-propen-3-ol, melting point 161° C.

The compounds listed in the table can be prepared as in Example 1.

TABLE I

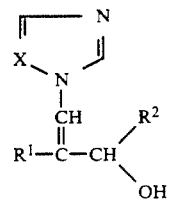

| Example | $R^1$ | $R^2$ | X | m.p./IR |
|---|---|---|---|---|
| 1 | 4-Cl—$C_6H_4$ | 2-$CF_3$—$C_6H_4$ | N | 161° C. |
| 2 | 4-Cl—$C_6H_4$ | 2-Cl—$C_6H_4$ | N | |
| 3 | 4-Cl—$C_6H_4$ | 2-F—$C_6H_4$ | N | |
| 4 | 4-Cl—$C_6H_4$ | 2-Br—$C_6H_4$ | N | |
| 5 | 4-Cl—$C_6H_4$ | 2-$CH_3$—$C_6H_4$ | N | 116-169° C. |
| 6 | 4-Cl—$C_6H_4$ | 2-$OCH_3$—$C_6H_4$ | N | 1491, 1245, 1091, 1015, 756 cm$^{-1}$ |
| 7 | 4-Cl—$C_6H_4$ | cyclopropyl | N | |
| 8 | 4-Cl—$C_6H_4$ | cyclopentyl | N | |
| 9 | 4-Cl—$C_6H_4$ | cyclohexyl | N | |
| 10 | 4-Cl—$C_6H_4$ | 4-tetrahydropyranyl | N | |
| 11 | 4-Cl—$C_6H_4$ | 3-pyridyl | N | |
| 12 | 4-Cl—$C_6H_4$ | $CH_3$ | N | |
| 13 | $C_6H_5$ | 2-$CF_3$—$C_6H_4$ | N | 172-174° C. |
| 14 | $C_6H_5$ | 2-Cl—$C_6H_4$ | N | |
| 15 | $C_6H_5$ | 2-F—$C_6H_4$ | N | |
| 16 | $C_6H_5$ | 2-Br—$C_6H_4$ | N | |
| 17 | $C_6H_5$ | 2-$CH_3$—$C_6H_4$ | N | |
| 18 | $C_6H_5$ | 2-$OCH_3$—$C_6H_4$ | N | |
| 19 | $C_6H_5$ | cyclopropyl | N | |
| 20 | $C_6H_5$ | cyclopentyl | N | |
| 21 | $C_6H_5$ | cyclohexyl | N | |
| 22 | $C_6H_5$ | 4-tetrahydropyranyl | N | |
| 23 | $C_6H_5$ | 3-pyridyl | N | |
| 24 | 4-F—$C_6H_4$ | 2-$CF_3$—$C_6H_4$ | N | |
| 25 | 4-F—$C_6H_4$ | 2-Cl—$C_6H_4$ | N | 159-160° C. |
| 26 | 4-F—$C_6H_4$ | 2-Cl—$C_6H_4$ | N × $CuCl_2$ | 181-185° C. |
| 27 | 4-F—$C_6H_4$ | 2-Cl—$C_6H_4$ | CH | 175-177° C. |
| 28 | 4-F—$C_6H_4$ | 2-F—$C_6H_4$ | N | |
| 29 | 4-F—$C_6H_4$ | 2-Br—$C_6H_4$ | N | 176-178° C. |
| 30 | 4-F—$C_6H_4$ | 2-$CH_3$—$C_6H_4$ | N | 116-168° C. |
| 31 | 4-F—$C_6H_4$ | 2-$OCH_3$—$C_6H_4$ | N | 78-80° C. |
| 32 | 4-F—$C_6H_4$ | cyclopropyl | N | |
| 33 | 4-F—$C_6H_4$ | cyclopentyl | N | |
| 34 | 4-F—$C_6H_4$ | cyclohexyl | N | |
| 35 | 4-F—$C_6H_4$ | 3-pyridyl | N | |
| 36 | 4-F—$C_6H_4$ | 4-tetrahydropyranyl | N | |
| 37 | 4-Br—$C_6H_4$ | 2-$CF_3$—$C_6H_4$ | N | |
| 38 | 4-Br—$C_6H_4$ | 2-F—$C_6H_4$ | N | |
| 39 | 4-Br—$C_6H_4$ | 2-Cl—$C_6H_4$ | N | |
| 40 | 4-Br—$C_6H_4$ | 2-Br—$C_6H_4$ | N | |
| 41 | 4-Br—$C_6H_4$ | 2-$CH_3$—$C_6H_4$ | N | |
| 42 | 4-Br—$C_6H_4$ | 2-$OCH_3$—$C_6H_4$ | N | |
| 43 | 4-Br—$C_6H_4$ | cyclopropyl | N | |
| 44 | 4-Br—$C_6H_4$ | cyclohexyl | N | |
| 45 | 2-F—$C_6H_4$ | 2-$CF_3$—$C_6H_4$ | N | |
| 46 | 2-F—$C_6H_4$ | 2-F—$C_6H_4$ | N | 104-106° C. |
| 47 | 2-F—$C_6H_4$ | 2-Cl—$C_6H_4$ | N | |
| 48 | 2-F—$C_6H_4$ | 2-Br—$C_6H_4$ | N | |
| 49 | 2-F—$C_6H_4$ | 2-$CH_3$—$C_6H_4$ | N | |
| 50 | 2-F—$C_6H_4$ | 2-$OCH_3$—$C_6H_4$ | N | |
| 51 | 2-F—$C_6H_4$ | cyclopentyl | N | |

TABLE-continued

| Example | R¹ | R² | X | m.p./IR |
|---|---|---|---|---|
| 52 | 2-F—C₆H₄ | cyclohexyl | N | |
| 53 | 2-Cl—C₆H₄ | 2-CF₃—C₆H₄ | N | |
| 54 | 2-Cl—C₆H₄ | 2-F—C₆H₄ | N | |
| 55 | 2-Cl—C₆H₄ | 2-Cl—C₆H₄ | N | |
| 56 | 2-Cl—C₆H₄ | 2-Br—C₆H₄ | N | |
| 57 | 2-Cl—C₆H₄ | 2-CH₃—C₆H₄ | N | |
| 58 | 2-Cl—C₆H₄ | 2-OCH₃—C₆H₄ | N | |
| 59 | 2-Cl—C₆H₄ | cyclopentyl | N | |
| 60 | 2-Cl—C₆H₄ | cyclohexyl | N | |
| 61 | 2-Br—C₆H₄ | 2-CF₃—C₆H₄ | N | |
| 62 | 2-Br—C₆H₄ | 2-F—C₆H₄ | N | |
| 63 | 2-Br—C₆H₄ | 2-Cl—C₆H₄ | N | |
| 64 | 2-Br—C₆H₄ | 2-Br—C₆H₄ | N | |
| 65 | 2-Br—C₆H₄ | 2-CH₃—C₆H₄ | N | |
| 66 | 2-Br—C₆H₄ | 2-OCH₃—C₆H₄ | N | |
| 67 | 2-Br—C₆H₄ | cyclohexyl | N | |
| 68 | 3-Cl—C₆H₄ | 2-CF₃—C₆H₄ | N | |
| 69 | 3-Cl—C₆H₄ | 2-F—C₆H₄ | N | |
| 70 | 3-Cl—C₆H₄ | 2-Cl—C₆H₄ | N | |
| 71 | 3-Cl—C₆H₄ | 2-Br—C₆H₄ | N | |
| 72 | 3-Cl—C₆H₄ | 2-CH₃—C₆H₄ | N | |
| 73 | 3-Cl—C₆H₄ | cyclohexyl | N | |
| 74 | 2,4-Cl₂—C₆H₃ | 2-CF₃—C₆H₄ | N | |
| 75 | 2,4-Cl₂—C₆H₃ | 2-F—C₆H₄ | N | |
| 76 | 2,4-Cl₂—C₆H₃ | 2-Cl—C₆H₄ | N | |
| 77 | 2,4-Cl₂—C₆H₃ | 2-Br—C₆H₄ | N | |
| 78 | 2,4-Cl₂—C₆H₃ | 2-CH₃—C₆H₄ | N | |
| 79 | 2,4-Cl₂—C₆H₃ | 2-OCH₃—C₆H₄ | N | |
| 80 | 2,4-Cl₂—C₆H₃ | 3-pyridyl | N | |
| 81 | 2,4-Cl₂—C₆H₃ | cyclopropyl | N | |
| 82 | 2,4-Cl₂—C₆H₃ | cyclopentyl | N | |
| 83 | 2,4-Cl₂—C₆H₃ | cyclohexyl | N | |
| 84 | 2,4-Cl₂—C₆H₃ | 4-tetrahydropyranyl | N | |
| 85 | 2-Cl-4-F—C₆H₃ | 2-CF₃—C₆H₄ | N | |
| 86 | 2-Cl-4-F—C₆H₃ | 2-CF₃—C₆H₄ | CH | |
| 87 | 2-Cl-4-F—C₆H₃ | 2-F—C₆H₄ | N | |
| 88 | 2-Cl-4-F—C₆H₃ | 2-Cl—C₆H₄ | N | |
| 89 | 2-Cl-4-F—C₆H₃ | 2-CH₃—C₆H₄ | N | |
| 90 | 2-CF₃—C₆H₄ | 2-CF₃—C₆H₄ | N | |
| 91 | 2-CF₃—C₆H₄ | 2-F—C₆H₄ | N | |
| 92 | 2-CF₃—C₆H₄ | 2-Cl—C₆H₄ | N | |
| 93 | 2-CF₃—C₆H₄ | 2-Br—C₆H₄ | N | |
| 94 | 2-CF₃—C₆H₄ | 2-CH₃—C₆H₄ | N | |
| 95 | 2-CF₃—C₆H₄ | 2-OCH₃—C₆H₄ | N | |
| 96 | 2-CF₃—C₆H₄ | 3-pyridyl | N | |
| 97 | 2-CF₃—C₆H₄ | cyclopropyl | N | |
| 98 | 2-CF₃—C₆H₄ | cyclopentyl | N | |
| 99 | 2-CF₃—C₆H₄ | cyclohexyl | N | |
| 100 | 2-CF₃—C₆H₄ | 4-tetrahydropyranyl | N | |
| 101 | 3-CF₃—C₆H₄ | 2-CF₃—C₆H₄ | N | |
| 102 | 3-CF₃—C₆H₄ | 2-F—C₆H₄ | N | |
| 103 | 3-CF₃—C₆H₄ | 2-Cl—C₆H₄ | N | |
| 104 | 3-CF₃—C₆H₄ | 2-Br—C₆H₄ | N | |
| 105 | 3-CF₃—C₆H₄ | 2-CH₃—C₆H₄ | N | |
| 106 | 3-CF₃—C₆H₄ | 2-OCH₃—C₆H₄ | N | |
| 107 | 4-CF₃—C₆H₄ | 2-CF₃—C₆H₄ | N | |
| 108 | 4-CF₃—C₆H₄ | 2-F—C₆H₄ | N | |
| 109 | 4-CF₃—C₆H₄ | 2-Cl—C₆H₄ | N | |
| 110 | 4-CF₃—C₆H₄ | 2-Br—C₆H₄ | N | |
| 111 | 4-CF₃—C₆H₄ | 2-CH₃—C₆H₄ | N | |
| 112 | 4-CF₃—C₆H₄ | 2-OCH₃—C₆H₄ | N | |
| 113 | 4-CF₃—C₆H₄ | cyclopentyl | N | |
| 114 | 4-CF₃—C₆H₄ | cyclohexyl | N | |
| 115 | 1-naphthyl | 2-Cl—C₆H₄ | N | |
| 116 | 1-naphthyl | 2-Br—C₆H₄ | N | |
| 117 | 1-naphthyl | 2-F—C₆H₄ | N | |
| 118 | 2-naphthyl | 2-F—C₆H₄ | N | |
| 119 | 2-naphthyl | 2-Cl—C₆H₄ | N | |
| 120 | 2-naphthyl | 2-Br—C₆H₄ | N | |
| 121 | 2-naphthyl | 2-CH₃—C₆H₄ | N | |

TABLE-continued

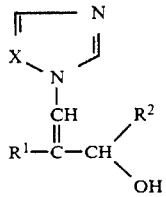

| Example | R$^1$ | R$^2$ | X | m.p./IR |
|---|---|---|---|---|
| 122 | 2-naphthyl | 2-OCH$_3$—C$_6$H$_4$ | N | |
| 123 | 2-naphthyl | cyclohexyl | N | |
| 124 | 4-biphenyl | 2-F—C$_6$H$_4$ | N | |
| 125 | 4-biphenyl | 2-Cl—C$_6$H$_4$ | N | |
| 126 | 4-biphenyl | 2-Br—C$_6$H$_4$ | N | |
| 127 | 4-CH$_3$—C$_6$H$_4$ | 2-CF$_3$—C$_6$H$_4$ | N | |
| 128 | 4-CH$_3$—C$_6$H$_4$ | 2-F—C$_6$H$_4$ | N | |
| 129 | 4-CH$_3$—C$_6$H$_4$ | 2-Cl—C$_6$H$_4$ | N | |
| 130 | 4-CH$_3$—C$_6$H$_4$ | 2-Br—C$_6$H$_4$ | N | |
| 131 | 4-CH$_3$—C$_6$H$_4$ | 2-CH$_3$—C$_6$H$_4$ | N | |
| 132 | 4-CH$_3$—C$_6$H$_4$ | 2-OCH$_3$—C$_6$H$_4$ | N | |
| 133 | 4-CH$_3$—C$_6$H$_4$ | cyclohexyl | N | |
| 134 | 2-CH$_3$—C$_6$H$_4$ | 2-F—C$_6$H$_4$ | N | |
| 135 | 2-CH$_3$—C$_6$H$_4$ | 2-Cl—C$_6$H$_4$ | N | |
| 136 | 2-CH$_3$—C$_6$H$_4$ | 2-OCH$_3$—C$_6$H$_4$ | N | |
| 137 | 2-OCH$_3$—C$_6$H$_4$ | 2-F—C$_6$H$_4$ | N | |
| 138 | 2-OCH$_3$—C$_6$H$_4$ | 2-Cl—C$_6$H$_4$ | N | |
| 139 | 2-OCH$_3$—C$_6$H$_4$ | 2-CH$_3$—C$_6$H$_4$ | N | |
| 140 | 4-OCH$_3$—C$_6$H$_4$ | 2-CF$_3$—C$_6$H$_4$ | N | |
| 141 | 4-OCH$_3$—C$_6$H$_4$ | 2-F—C$_6$H$_4$ | N | |
| 142 | 4-OCH$_3$—C$_6$H$_4$ | 2-Cl—C$_6$H$_4$ | N | |
| 143 | 4-OCH$_3$—C$_6$H$_4$ | 2-Br—C$_6$H$_4$ | N | |
| 144 | 4-OCH$_3$—C$_6$H$_4$ | 2-CH$_3$—C$_6$H$_4$ | N | |
| 145 | 4-NO$_2$—C$_6$H$_4$ | 2-F—C$_6$H$_4$ | N | |
| 146 | 4-NO$_2$—C$_6$H$_4$ | 2-Cl—C$_6$H$_4$ | N | |
| 147 | 4-NO$_2$—C$_6$H$_4$ | 2-CH$_3$—C$_6$H$_4$ | N | |
| 148 | 4-NH$_2$—C$_6$H$_4$ | 2-F—C$_6$H$_4$ | N | |
| 149 | 4-NH$_2$—C$_6$H$_4$ | 2-Cl—C$_6$H$_4$ | N | |
| 150 | 4-C$_6$H$_5$O—C$_6$H$_4$ | 2-F—C$_6$H$_4$ | N | |
| 151 | 4-C$_6$H$_5$O—C$_6$H$_4$ | 2-Cl—C$_6$H$_4$ | N | |
| 152 | 4-C$_6$H$_5$O—C$_6$H$_4$ | 2-Br—C$_6$H$_4$ | N | |
| 153 | 4-C$_6$H$_5$O—C$_6$H$_4$ | 2-CH$_3$—C$_6$H$_4$ | N | |
| 154 | 4-C$_6$H$_5$O—C$_6$H$_4$ | 2-CF$_3$—C$_6$H$_4$ | N | |
| 155 | 4-C$_6$H$_5$O—C$_6$H$_4$ | 2-OCH$_3$—C$_6$H$_4$ | N | |
| 156 | 4-C$_6$H$_5$O—C$_6$H$_4$ | cyclohexyl | N | |
| 157 | CH$_3$ | C$_6$H$_5$ | N | |
| 158 | CH$_3$ | 2-F—C$_6$H$_4$ | N | |
| 159 | CH$_3$ | 3-F—C$_6$H$_4$ | N | |
| 160 | CH$_3$ | 4-F—C$_6$H$_4$ | N | |
| 161 | CH$_3$ | 2-Cl—C$_6$H$_4$ | N | |
| 162 | CH$_3$ | 3-Cl—C$_6$H$_4$ | N | |
| 163 | CH$_3$ | 4-Cl—C$_6$H$_4$ | N | |
| 164 | CH$_3$ | 2-Br—C$_6$H$_4$ | N | |
| 165 | CH$_3$ | 4-Br—C$_6$H$_4$ | N | |
| 166 | CH$_3$ | 2-CH$_3$—C$_6$H$_4$ | N | |
| 167 | CH$_3$ | 4-CH$_3$—C$_6$H$_4$ | N | |
| 168 | CH$_3$ | 2,4-(CH$_3$)$_2$—C$_6$H$_3$ | N | |
| 169 | CH$_3$ | 4-tert.-C$_4$H$_9$—C$_6$H$_4$ | N | |
| 170 | CH$_3$ | 2-OCH$_3$—C$_6$H$_4$ | N | |
| 171 | CH$_3$ | 1-naphthyl | N | |
| 172 | CH$_3$ | 2-naphthyl | N | |
| 173 | CH$_3$ | 4-biphenyl | N | |
| 174 | CH$_3$ | 2,4-Cl$_2$—C$_6$H$_3$ | N | |
| 175 | CH$_3$ | 2-Cl-4-F—C$_6$H$_3$ | N | |
| 176 | CH$_3$ | 3-NO$_2$—C$_6$H$_4$ | N | |
| 177 | CH$_3$ | 4-NH$_2$—C$_6$H$_4$ | N | |
| 178 | CH$_3$ | cyclohexyl | N | |
| 179 | tert.-C$_4$H$_9$ | C$_6$H$_5$ | N | |
| 180 | tert.-C$_4$H$_9$ | 2-F—C$_6$H$_4$ | N | |
| 181 | tert.-C$_4$H$_9$ | 2-Cl—C$_6$H$_4$ | N | |
| 182 | tert.-C$_4$H$_9$ | 2-Br—C$_6$H$_4$ | N | |
| 183 | tert.-C$_4$H$_9$ | 3-F—C$_6$H$_4$ | N | |
| 184 | tert.-C$_4$H$_9$ | 3-Cl—C$_6$H$_4$ | N | |
| 185 | tert.-C$_4$H$_9$ | 4-F—C$_6$H$_4$ | N | |
| 186 | tert.-C$_4$H$_9$ | 4-Cl—C$_6$H$_4$ | N | 2963, 1505, 1488, 1275, 1014, 844 cm$^{-1}$ |
| 187 | tert.-C$_4$H$_9$ | 2-CH$_3$—C$_6$H$_4$ | N | |
| 188 | tert.-C$_4$H$_9$ | 4-CH$_3$—C$_6$H$_4$ | N | |
| 189 | tert.-C$_4$H$_9$ | 2,4-(CH$_3$)$_2$—C$_6$H$_3$ | N | |
| 190 | tert.-C$_6$H$_9$ | 4-tert.-C$_4$H$_9$—C$_6$H$_4$ | N | |

TABLE-continued $$\begin{array}{c} \phantom{X}\overset{\displaystyle N}{\underset{\displaystyle N}{\overbrace{\phantom{XXXX}}}} \\ X \phantom{XXX} \underset{\displaystyle |}{N} \\ \phantom{XXXXX} \underset{\displaystyle \|}{CH} \phantom{X} R^2 \\ R^1-\underset{\displaystyle \phantom{|}}{C}-CH \\ \phantom{XXXXXXXX} \diagdown OH \end{array} \qquad I$$

| Example | R$^1$ | R$^2$ | X | m.p./IR |
|---|---|---|---|---|
| 191 | tert.-C$_4$H$_9$ | 2-OCH$_3$—C$_6$H$_4$ | N | |
| 192 | tert.-C$_4$H$_9$ | 2,4-Cl$_2$—C$_6$H$_3$ | N | |
| 193 | tert.-C$_4$H$_9$ | 2-naphthyl | N | |
| 194 | tert.-C$_4$H$_9$ | cyclopentyl | N | |
| 195 | tert.-C$_4$H$_9$ | cyclohexyl | N | |
| 196 | cyclohexyl | C$_6$H$_5$ | N | |
| 197 | cyclohexyl | 2-F—C$_6$H$_4$ | N | |
| 198 | cyclohexyl | 3-F—C$_6$H$_4$ | N | |
| 199 | cyclohexyl | 4-F—C$_6$H$_4$ | N | |
| 200 | cyclohexyl | 2-Cl—C$_6$H$_4$ | N | |
| 201 | cyclohexyl | 3-Cl—C$_6$H$_4$ | N | |
| 202 | cyclohexyl | 4-Cl—C$_6$H$_4$ | N | 94° C. |
| 203 | cyclohexyl | 2-Br—C$_6$H$_4$ | N | |
| 204 | cyclohexyl | 2-CH$_3$—C$_6$H$_4$ | N | |
| 205 | cyclohexyl | 4-CH$_3$—C$_6$H$_4$ | N | |
| 206 | cyclohexyl | 2,4(CH$_3$)$_2$—C$_6$H$_3$ | N | |
| 207 | cyclohexyl | 2-CF$_3$—C$_6$H$_4$ | N | |
| 208 | cyclohexyl | 3-CF$_3$—C$_6$H$_4$ | N | |
| 209 | cyclohexyl | 4-CF$_3$—C$_6$H$_4$ | N | |
| 210 | cyclohexyl | 4-tert.-C$_4$H$_9$—C$_6$H$_4$ | N | |
| 211 | cyclohexyl | 2-OCH$_3$—C$_6$H$_4$ | N | |
| 212 | cyclohexyl | 2,4-Cl$_2$—C$_6$H$_3$ | N | 112–115° C. |
| 213 | cyclohexyl | 2-naphthyl | N | |
| 214 | cyclohexyl | 4-biphenyl | N | |
| 215 | cyclohexyl | 2-Cl-4-F—C$_6$H$_3$ | N | |
| 216 | cyclohexyl | cyclohexyl | N | |
| 217 | 4-tetrahydropyranyl | C$_6$H$_5$ | N | |
| 218 | 4-tetrahydropyranyl | 2-F—C$_6$H$_4$ | N | |
| 219 | 4-tetrahydropyranyl | 3-F—C$_6$H$_4$ | N | |
| 220 | 4-tetrahydropyranyl | 4-F—C$_6$H$_4$ | N | |
| 221 | 4-tetrahydropyranyl | 2-Cl—C$_6$H$_4$ | N | |
| 222 | 4-tetrahydropyranyl | 3-Cl—C$_6$H$_4$ | N | |
| 223 | 4-tetrahydropyranyl | 4-Cl—C$_6$H$_4$ | N | 164–166° C. |
| 224 | 4-tetrahydropyranyl | 2-Br—C$_6$H$_4$ | N | |
| 225 | 4-tetrahydropyranyl | 4-Br—C$_6$H$_4$ | N | |
| 226 | 4-tetrahydropyranyl | 2-CH$_3$—C$_6$H$_4$ | N | |
| 227 | 4-tetrahydropyranyl | 4-CH$_3$—C$_6$H$_4$ | N | |
| 228 | 4-tetrahydropyranyl | 2,4-(CH$_3$)$_2$—C$_6$H$_3$ | N | |
| 229 | 4-tetrahydropyranyl | 2-OCH$_3$—C$_6$H$_4$ | N | |
| 230 | 4-tetrahydropyranyl | 2,4-Cl$_2$—C$_6$H$_3$ | N | |
| 231 | 4-tetrahydropyranyl | 2-naphthyl | N | |
| 232 | 4-tetrahydropyranyl | 4-biphenyl | N | |
| 233 | 4-tetrahydropyranyl | cyclohexyl | N | |

In general terms, the novel compounds are extremely effective on a broad spectrum of phytopathogenic fungi, in particular those from the class consisting of the Ascomycetes and Basidiomycetes. Some of them have a systemic action and can be used as foliar and soil fungicides.

The fungicidal compounds are of particular interest for controlling a large number of fungi in various crops or their seeds, especially wheat, rye, barley, oats, rice, Indian corn, lawns, cotton, soybeans, coffee, sugar cane, fruit and ornamentals in horticulture and viticulture, and in vegetables such as cucumbers, beans and cucurbits.

The novel compounds are particularly useful for controlling the following plant diseases:
Erysiphe graminis in cereals,
Erysiphe cichoracearum and Sphaerotheca fuliginea in cucurbits,
Podosphaera leucotricha in apples,
Uncinula necator in vines,
Puccinia species in cereals,
Rhizoctonia solani in cotton,
Ustilago species in cereals and sugar cane,
Venturia inaequalis (scab) in apples,
Helminthosporium species in cereals,
Septoria nodorum in wheat,
Botrytis cinerea (gray mold) in strawberries and grapes,
Cercospora arachidicola in groundnuts,
Pseudocercosporelia herpotrichoides in wheat and barley,
Pyricularia oryzae in rice,
Phytophthora infestans in potatoes and tomatoes,
Fusarium and Verticillium species in various plants,
Plasmopara viticola in grapes,
Alternaria species in fruit and vegetables.

The compounds are applied by spraying or dusting the plants with the active ingredients, or treating the seeds of the plants with ingredients. They may be applied before or after infection of the plants or seeds by the fungi.

The novel compounds may exercise a variety of influences on practically all plant development stages, and are therefore used as growth regulators. The diversity of action of growth regulators depends especially on
a) the type and variety of plant;
b) the time applied, with reference to the development stage of the plants and the time of the year;
c) the place and method of application (seed treatment, soil treatment, or application to foliage);
d) climatic factors, e.g., average temperature, amount of precipitation, sunshine and duration;
e) soil conditions (including fertilization);
f) the formulation of the active ingredient; and
g) the concentration at which the active ingredient is applied.

A description of some of the various possibilities of using the growth regulators according to the invention in agriculture and horticulture is given below.

A. vegetative plant growth can be inhibited to a considerable extent, a fact which is manifested particularly in a reduction in plant height. The treated plants thus have a compact habit; furthermore, the leaf color is darker.

Of advantage in practice is for example the reduction in grass growth on roadsides, hedges, canal embankments and on areas such as parks, sportsgrounds, fruit orchards, lawns and airfields, thus reducing expensive and time-consuming mowing.

A further feature of economic interest is the increase in the rigor of crops which tend to lodge, such as cereals, Indian corn, sunflowers and soybeans. The shortening and strengthening of the stem thus caused reduces or eliminates the danger of lodging under unfavorable weather conditions.

The use of growth regulators is also important for inhibiting plant height and changing the time of ripening in cotton. It is thus possible for this important crop to be harvested completely mechanically.

Growth regulators may also increase or inhibit lateral branching. This is of interest when, for instance in tobacco plants, it is desired to inhibit the formation of lateral shoots (suckers) in favor of leaf development.

With growth regulators, it is possible for instance in winter rape to considerably increase the resistance to freeze injury. On the one hand, upward growth and the development of a too luxuriant (and thus particularly frost-susceptible) leaf or plant mass are inhibited; on the other, the young rape plants are kept, in spite of favorable growth conditions, in the vegetative development stage before winter frosts begin. The danger of freeze injury is thus eliminated in plants which tend to lose prematurely their inhibition to bloom and pass into the generative phase. In other crops, too, e.g., winter cereals, it is advantageous if the plants are well tillered in the fall as a result of treatment with the compounds according to the invention, but enter winter with not too lush a growth. This is a preventive measure against increased susceptibility to freeze injury and—because of the relatively low leaf or plant mass—attack by various (especially fungus) diseases. The inhibition of vegetative growth also makes closer planting possible in numerous crops, which means an increase in yield, based on the area cropped.

B. Better yields both of plant parts and plant materials may be obtained with the novel agents. It is thus for instance possible to induce increased formation of buds, blossom, leaves, fruit, seed grains, roots and tubers, to increase the sugar content of sugarbeets, sugarcane and citrus fruit, to raise the protein content of cereals and soybeans, and to stimulate the increased formation of latex in rubber trees.

The compounds of the formula I may raise the yield by influencing plant metabolism or by promoting or inhibiting vegetative and/or generative plant growth.

C. It is also possible with growth regulators to shorten or lengthen growth stages and to accelerate or retard the ripening process in plant parts either before or after harvesting.

A factor of economic interest is for example the facilitation of harvesting made possible by a chemical, temporally concentrated loosening (abscission) of the adherence of stalks to the branches of citrus fruit, olive trees, and other kinds of pomes, drupes and indehiscent fruit. The same mechanism, i.e., promotion of the formation of separation layers between fruit or leaf and stem of the plant, is also essential for a readily controllable defoliation of crop plants.

Further, transpiration in crop plants may be reduced with growth regulators. This is particularly important for plants growing in agricultural areas which are expensive to irrigate. e.g., in arid or semi-arid areas. Irrigation frequency can be reduced by using the compounds according to the invention, making for lower costs. As a result of the use of growth regulators, the water available can be better utilized, because, inter alia,
the size of the stomata opening is reduced;
a thicker epidermis and cuticle are formed;
penetration of the soil by the roots is improved;
the micro-climate in the stand is favorably influenced by the more compact growth.

The active ingredients according to the invention may be applied not only to the seed as a dressing, but also to the soil, i.e., via the roots, and to the foliage by spraying.

As a result of the good tolerance by crop plants, the application rate when the active ingredients are used as growth regulators may vary within wide limits.

When the active ingredients are used for treating seed, amounts of from 0.001 to 50, and preferably from 0.01 to 10 g per kg of seed are generally required. For foliage and soil treatment, amounts of from 0.01 to 10, preferably from 0.02 to 3, kg/ha are generally considered to be sufficient.

The novel substances can be converted into conventional formulations such as solutions, emulsions, suspensions, dusts, powders, pastes and granules. The application forms depend entirely on the purposes for which they are intended; they should at all events ensure a fine and uniform distribution of the active ingredient. The formulations are produced in known manner, for example by extending the active ingredient with solvents and/or carriers, with or without the use of emulsifiers and dispersants; if water is used as solvent, it is also possible to employ other organic solvents as auxiliary solvents. Suitable auxiliaries for this purpose are solvents such as aromatics (e.g., xylene), chlorinated aromatics (e.g., chlorobenzenes), paraffins (e.g., crude oil fractions), alcohols (e.g., methanol, butanol), ketones (e.g., cyclohexanone), amines (e.g., ethanolamine, dimethylformamide), and water; carriers such as ground natural minerals (e.g., kaolins, aluminas, talc and chalk) and ground synthetic minerals (e.g., highly disperse silica and silicates); emulsifiers such as nonionic and anionic emulsifiers (e.g., polyoxyethylene fatty alcohol ethers, alkyl sulfonates and aryl sulfonates); and dispersants such as lignin, sulfite waste liquors and methylcellulose.

The fungicides generally contain from 0.1 to 95, and preferably from 0.5 to 90, wt % of active ingredient. The application rates are from 0.02 to 3 kg or more of active ingredient per hectare, depending on the type of effect desired. The novel compounds may also be used for protecting materials, e.g., on Paecilomyces variotii.

The agents and the ready-to-use formulations prepared from them, such as solutions, emulsions, suspensions, powders, dusts, pastes and granules, are applied in conventional manner, for example by spraying, atomizing, dusting, scattering, dressing or watering.

Examples of formulations are given below.

I. A solution of 90 parts by weight of compound no. 25 is mixed with 10 parts by weight of N-methyl-α-pyrrolidone, which is suitable for application in the form of very fine drops.

II. A mixture of 20 parts by weight of compound no. 27, 80 parts by weight of xylene, 10 parts by weight of the adduct of 8 to 10 moles of ethylene oxide and 1 mole of oleic acid-N-monoethanolamide, 5 parts by weight of the calcium salt of dodecylbenzenesulfonic acid, and 5 parts by weight of the adduct of 40 moles of ethylene oxide and 1 mole of castor oil. By finely dispersing the mixture in water, an aqueous dispersion is obtained.

III. An aqueous dispersion of 20 parts by weight of compound no. 25, 40 parts by weight of cyclohexanone, 30 parts by weight of isobutanol, 20 parts by weight of the adduct of 40 moles of ethylene oxide and 1 mole of castor oil. By pouring the solution into water and finely distributing it therein, an aqueous dispersion is obtained.

IV. An aqueous dispersion of 20 parts by weight of compound no. 27, 25 parts by weight of cyclohexanol, 65 parts by weight of a mineral oil fraction having a boiling point between 210° and 280° C., and 10 parts by weight of the adduct of 40 moles of ethylene oxide and 1 mole of castor oil. By pouring the solution into water and finely distributing it therein, an aqueous dispersion is obtained.

V. A hammer-milled mixture of 80 parts by weight of compound no. 25, 3 parts by weight of the sodium salt of diisobutylnaphthalene-α-sulfonic acid, 10 parts by weight of the sodium salt of a lignin-sulfonic acid obtained from a sulfite waste liquor, and 7 parts by weight of powdered silica gel. By finely dispersing the mixture in water, a spray liquor is obtained.

VI. An intimate mixture of 3 parts by weight of compound no. 27 and 97 parts by weight of particulate kaolin. The dust contains 3 wt % of the active ingredient.

VII. An intimate mixture of 30 parts by weight of compound no. 25, 92 parts by weight of powdered silica gel and 8 parts by weight of paraffin oil sprayed onto the surface of this silica gel. This formulation of the active ingredient exhibits good adherence.

VIII. A stable aqueous dispersion of 40 parts by weight of compound no. 27, 10 parts of the sodium salt of a phenolsulfonic acid-urea-formaldehyde condensate, 2 parts of silica gel and 48 parts of water, which dispersion can be further diluted.

IX. A stable oily dispersion of 20 parts by weight of compound no. 25, 2 parts by weight of the calcium salt of dodecylbenzenesulfonic acid, 8 parts by weight of a fatty alcohol polyglycol ether, 2 parts by weight of the sodium salt of a phenolsulfonic acid-urea-formaldehyde condensate and 68 parts by weight of a paraffinic mineral oil.

In these application forms, the agents according to the invention may also be present together with other active ingredients, for example herbicides, insecticides, growth regulators, and fungicides, and may furthermore be mixed and applied together with fertilizers. Admixture with other fungicides frequently results in a greater fungicidal action spectrum.

USE EXAMPLES

The active ingredients 1-(1,2,4-triazol-1-yl)-2-(4-chlorophenyl)-3-(2,4-dichlorophenyl)-1-propen-3-ol (A) and 1-(1,2,4-triazol-1-yl)-2-(4-chlorophenyl)-3-phenyl-1-propen-3-ol (B) disclosed in EP 23,286 were used for comparison purposes.

USE EXAMPLE 1

Action on *Pyrenophora teres*

Barley seedlings of the "Igri" variety were sprayed to runoff at the 2-leaf stage with aqueous suspensions containing (dry basis) 80% of active ingredient and 20% emulsifier. After 24 hours the plants were inoculated with a spore suspension of the fungus Pyrenophora teres and placed for 48 hours in a high-humidity climatic cabinet kept at 18° C. The plants were then cultivated for a further 5 days in the greenhouse at 20°–22° C. and a relative humidity of 70%. The extent of fungus spread was then determined.

The results show that active ingredients 25 and 27, applied as 0.05 wt % spray liquors, had a better fungicidal action (90%) than prior art comparative agents A and B (30%).

USE EXAMPLE 2

To determine the growth-regulating properties of the candidate compounds, test plants were grown in a culture medium provided with sufficient nutrients in plastic pots approx. 12.5 cm in diameter.

In the preemergence method, the candidate compounds were sprayed as aqueous formulations onto the seedbed on the day of sowing.

In the postemergence method, the candidate compounds were sprayed as aqueous formulations onto the plants. The growth-regulating action observed was confirmed at the end of the experiment by measuring the height of the plants. The figures obtained were compared with the growth height of the untreated plants.

The reduction in growth height was also accompanied by a deeper leaf coloration. The increased chlorophyll content is indicative of an increased rate of photosynthesis, making for bigger yields.

The individual data are given in the following tables.

TABLE 1

| | Spring wheat "Ralle" Postemergence (leaf) treatment | |
|---|---|---|
| Active ingr. | mg of a.i. per vessel | Growth height relative |
| untreated | — | 100 |
| B | 6 | 100 |
| A | 6 | 100 |
| 186 | 6 | 83.4 |

TABLE 2

| | Spring barley "Aramir" Preemergence treatment | |
|---|---|---|
| Active ingr. | Conc. mg of a.i./vessel | Growth height relative |
| untreated | — | 100 |
| B | 6 | 47.7* |
| A | 6 | 100 |
| 25 | 6 | 24.9 |
| 186 | 6 | 27.1 |
| 202 | 6 | 33.2 |
| 212 | 6 | 33.2 |

*significant leaf damage

TABLE 3

| | Spring rape "Petranova" Preemergence treatment | |
|---|---|---|
| Active ingr. | Conc. mg of a.i./vessel | Growth height relative |
| untreated | — | 100 |
| B | 6 | 86.5* |
| A | 6 | 100 |
| 186 | 6 | 70.2 |

*heavy leaf damage

TABLE 4

| | Spring rape "Petranova" Postemergence (leaf) treatment | |
|---|---|---|
| Active ingr. | Conc. mg of a.i./vessel | Growth height relative |
| untreated | — | 100 |
| B | 6 | 81.1* |
| A | 6 | 86.6 |
| 186 | 6 | 74.3 |

*significant leaf damage

We claim:

1. A compound of the formula I

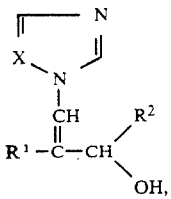

where $R^1$ is $C_1$–$C_8$-alkyl, $C_3$–$C_8$-cycloalkyl, tetrahydropyranyl, or naphthyl, these radicals being unsubstituted or mono- or trisubstituted by halogen, nitro, phenoxy, amino, alkyl, alkoxy or haloalkyl, each of 1 to 4 carbon atoms, or $R^1$ is 4-fluorophenyl; $R^2$ is 2-chlorophenyl, 2-bromophenyl, 4-chlorophenyl or 2,4-dichlorophenyl; and X is N, or a plant-tolerated acid addition salt or metal complex thereof.

2. A compound of claim 1 wherein $R^1$ is 4-fluorophenyl and $R^2$ is 2-chlorophenyl.

3. A compound of claim 1 wherein $R^1$ is 4-fluorophenyl and $R^2$ is 2-bromophenyl.

4. A fungicidal composition containing an inert carrier and fungicidally effective amount of a compound of claim 1.

5. A process for combating fungi, wherein a fungicidally effective amount of a compound of claim 1 is allowed to act on the fungi, or the plant materials, plant areas, plants or seed threatened by fungus attack.

6. A compound according to claim 1 wherein $R^1$ is t-butyl and $R^2$ is 4-chlorophenyl.

7. A compound of claim 1 wherein $R^1$ is cyclohexyl and $R^2$ is 4-chlorophenyl.

8. A compound of claim 1 wherein $R^1$ is cyclohexyl and $R^2$ is 2,4-dichlorophenyl.

* * * * *